(12) United States Patent
Sullivan

(10) Patent No.: US 7,486,990 B2
(45) Date of Patent: Feb. 3, 2009

(54) ELECTROCARDIOGRAM MONITORING AND CARDIAC THERAPY PULSE DELIVERY SYSTEM AND METHOD

(75) Inventor: Joseph L. Sullivan, Kirkland, WA (US)

(73) Assignee: MedTronic Physio-Control Manufacturing Corporation, Redmond, WA (US)

( * ) Notice: Subject to any disclaimer, the term of this patent is extended or adjusted under 35 U.S.C. 154(b) by 0 days.

(21) Appl. No.: 10/423,602

(22) Filed: Apr. 24, 2003

(65) Prior Publication Data

US 2004/0215271 A1    Oct. 28, 2004

(51) Int. Cl.
*A61N 1/08* (2006.01)
(52) U.S. Cl. .............................. 607/27; 607/11; 600/510
(58) Field of Classification Search .................. 600/510, 600/515; 607/4, 10
See application file for complete search history.

(56) References Cited

U.S. PATENT DOCUMENTS

| 4,955,381 | A |  | 9/1990 | Way et al. |
| 5,080,099 | A |  | 1/1992 | Way et al. |
| 5,405,362 | A | * | 4/1995 | Kramer et al. ................. 607/5 |
| 6,148,233 | A | * | 11/2000 | Owen et al. .................... 607/5 |
| 6,595,987 | B1 | * | 7/2003 | Negus et al. .................. 606/14 |
| 2001/0051821 | A1 |  | 12/2001 | Synder |
| 2004/0088016 | A1 | * | 5/2004 | Daum et al. .................. 607/19 |

* cited by examiner

*Primary Examiner*—Robert E. Pezzuto
*Assistant Examiner*—Tammie K. Heller

(57) ABSTRACT

A cardiac therapy pulse delivery system includes a plurality of electrodes, an ECG signal processor circuit, and a pulse generator circuit. Each of the electrodes has at least one therapy element and at least one monitor element that are electrically insulated from one another. The ECG signal processor circuit is electrically coupled to each monitor element on each electrode and is operable to convert ECG signals detected by the monitor elements into ECG data. The cardiac pulse generator circuit is electrically coupled to each therapy element on each electrode and is operable to supply one or more cardiac therapy pulses thereto.

3 Claims, 3 Drawing Sheets

ELECTROCARDIOGRAM MONITORING AND CARDIAC THERAPY PULSE DELIVERY SYSTEM AND METHOD

FIELD OF THE INVENTION

The present invention generally relates to cardiac therapy pulse delivery systems and, more particularly, to a system and method that provides improved electrocardiogram (ECG) monitoring capabilities during cardiac therapy pulse delivery, such as defibrillation and/or transthoracic pacing.

BACKGROUND OF THE INVENTION

The heart includes a natural electrical system that generates electrical impulses, which cause the heart to contract. When functioning properly, the electrical impulses generated in the heart cause the heart to beat in a coordinated fashion. If, however, the heart's electrical system malfunctions, the heart will not beat in a coordinated fashion, which can result in various types of cardiac arrhythmias.

Cardiac arrhythmias can be classified into two general categories, bradycardia and tachycardia. Bradycardia is an abnormally slow or unsteady heart rate, whereas tachycardia is an abnormally fast heart rate. Tachycardia arrhythmias may be further classified into two general subcategories, supraventricular tachycardia and ventricular tachycardia. There are various types of supraventricular tachycardias, including atrial fibrillation (AF) and atrial flutter. There are also various types of ventricular tachycardias (VT), which include "pulseless VT," "VT with pulse," and ventricular fibrillation (VF).

Many cardiac arrhythmias can be treated by delivering an electrical pulse to, or in the vicinity of, the heart. The magnitude, duration, and number of electrical pulses that are delivered may, in many instances, depend upon the type of cardiac arrhythmia being experienced. For example, defibrillation pulses, which are relatively high in magnitude, may be used to treat, for example, VF, and pulseless VT arrhythmias, whereas pacing pulses, which are of a relatively lesser magnitude than defibrillation pulses, may be used to treat, for example, VT with pulse, AF, and atrial flutter arrhythmias, and bradycardia arrhythmias.

Various types of implantable devices are available to generate and deliver the various types of electrical pulses described above. However, not all individuals that experience a cardiac arrhythmia have such a device implanted. Thus, various types of external defibrillators have been designed and manufactured, including both manual and automated external defibrillators (AEDs). Most external defibrillators, both manual and automatic, include electrical pulse generation circuitry and a pair of pulse delivery electrodes. The electrical pulse generation circuitry generates a therapy pulse that may be applied to a patient via the pair of pulse delivery electrodes, when the pulse delivery electrodes are positioned on the patient's chest. With a manual defibrillator, the energy level of the therapy pulse applied to a patient may be manually adjusted. With an AED, the energy level of a therapy pulse may preferably be adjusted automatically, though in some cases the energy level may be also adjusted manually. In either case, the energy level of the therapy pulse to be applied will depend on whether the patient needs to receive, for example, a defibrillation pulse or one or more pacing pulses.

No matter the type of therapy pulse a defibrillator delivers to a patient, it is highly desirable that the patient's ECG be monitored after the therapy pulse is delivered. That way a meaningful determination can be made as to whether the patient needs one or more subsequent therapy pulses, and the energy level at which each subsequent pulse should be delivered. Generally, when an external defibrillator is being used, a patient's ECG is monitored in one of two ways. If the external defibrillator is a manual defibrillator, separate ECG monitoring electrodes may be applied to the patient. If the external defibrillator is an AED, the patient's ECG may be monitored via the pulse delivery electrodes or, in some instances, using separate ECG monitoring electrodes. It would be preferable if a patient's ECG could be monitored via the pulse delivery electrodes, no matter the type of defibrillator being used or the energy level of the defibrillator pulse being applied; however, for at least the following reasons, this is presently not practical.

Cardiac therapy pulses can range from a few hundred volts (for pacing pulses) up to a few thousand volts (for defibrillation pulses). Thus, when a cardiac therapy pulse is delivered to a patient, the electrodes accumulate an electrical charge. This electrical charge gradually decays after the pulse is delivered, but this decay can take from several hundreds of milliseconds (for a pacing pulse) up to several seconds (for a defibrillation pulse). An ECG signal, which may be only a few millivolts in magnitude, may be generated approximately 100 milliseconds (or less) after a cardiac therapy pulse is delivered. However, because of the relatively large electrical charge that has accumulated on the pulse delivery electrodes, this ECG signal may not be detectable via the pulse delivery electrodes until the accumulated charge has sufficiently decayed.

Thus, manual defibrillators are presently not useful for administering periodic transthoracic pacing pulses to a patient, unless additional ECG monitoring leads are also applied to the patient. Moreover, present AEDs that are not equipped with separate ECG monitoring leads are not capable of accurately detecting ECG signals after a therapy pulse has been delivered, until the accumulated charge on the pulse delivery electrodes has sufficiently decayed. The time it takes for the accumulated charge to decay, can result in an undesirable delay in the delivery of a subsequent therapy pulse, or can delay a decision to administer cardiopulmonary resuscitation (CPR). Although additional ECG monitoring electrodes can, and sometimes are, provided with manual defibrillators and AEDs, it would be preferable if such leads could be eliminated, most notably for AEDs, since the medical skill level of persons operating AEDs may not be high.

Hence, there is a need for a system and method of monitoring ECG signals during cardiac therapy pulse delivery that does not rely on additional ECG monitoring leads and/or allows detection of ECG signals substantially immediately after a cardiac therapy pulse has been delivered without the use of additional ECG monitoring leads. The present invention addresses these needs. Furthermore, other desirable features and characteristics of the present invention will become apparent from the subsequent detailed description and the appended claims, taken in conjunction with the accompanying drawings and this background.

BRIEF SUMMARY OF THE INVENTION

A system and method of monitoring electrocardiogram (ECG) signals during cardiac therapy pulse delivery is provided that does not rely on additional ECG monitoring leads. The system and method also allows detection of ECG signals substantially immediately after a cardiac therapy pulse has been delivered.

In one embodiment, and by way of example only, a method of monitoring ECG signals during cardiac therapy pulsing includes applying two or more electrodes to a patient. Each electrode has at least a therapy element and a monitor element coupled thereto. One or more cardiac therapy pulses are supplied to the therapy element on each of the applied electrodes. One or more ECG signals are monitored via the monitor element on each of the applied electrodes.

In another exemplary embodiment, a cardiac electrical pulse therapy delivery system includes a plurality of electrodes, an ECG signal processor circuit, and a pulse generator circuit. Each electrode has at least one therapy element and one monitor element electrically that are electrically insulated from one another. The ECG signal processor circuit is electrically coupled to the monitor element on each electrode and is operable to convert ECG signals detected by the monitor elements into ECG data. The cardiac pulse generator circuit is electrically coupled to the electrode therapy element on each electrode and operable to supply one or more cardiac therapy pulses thereto.

In still another exemplary embodiment, a method of monitoring electrocardiogram (ECG) signals during transthoracic pacing includes applying two electrodes to a patient, and supplying one or more pacing pulses to the patient via the electrodes, whereby at least a portion of the electrodes accumulate an electrical charge that decays after each pulse is supplied. One or more ECG signals are monitored via the electrodes before the accumulated electrical charge on each electrode has decayed.

In yet still another exemplary embodiment, a system for monitoring electrocardiogram (ECG) signals during transthoracic pacing includes electrode means, ECG signal processing means, and pacing pulse generation means. The electrode means are for (i) receiving and applying one or more pacing pulses and (ii) sensing one or more ECG signals. The ECG signal processing means is for converting the ECG signals detected by the electrode means into ECG data. The pacing pulse generation means is for supplying one or more pacing pulses to the electrode means.

BRIEF DESCRIPTION OF THE DRAWINGS

The present invention will hereinafter be described in conjunction with the following drawing figures, wherein like numerals denote like elements, and wherein.

DETAILED DESCRIPTION OF A PREFERRED EMBODIMENT

The following detailed description is merely exemplary in nature and is not intended to limit the invention or the application and uses of the invention. Furthermore, there is no intention to be bound by any theory presented in the preceding background of the invention or the following detailed description. In this regard, although the present embodiment is, for convenience of explanation, depicted and described as being implemented in an automatic external defibrillator (AED), it will be appreciated that it can be implemented in other cardiac therapy pulse delivery systems such as, for example, manual defibrillators.

Figure 1:
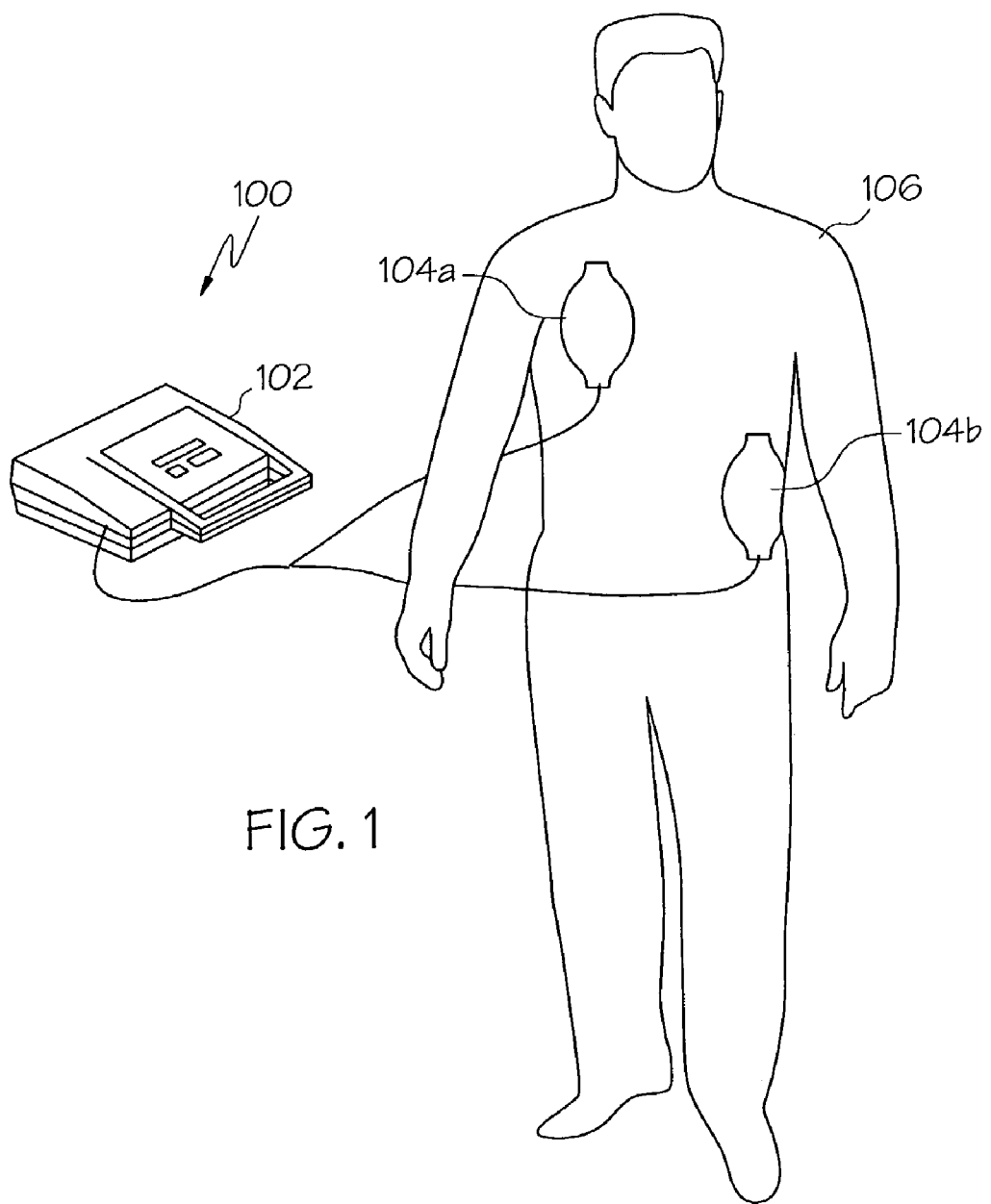
FIG. 1 is an exemplary external defibrillator that may be configured to operate in accordance with an the present invention.

An exemplary cardiac pulse therapy delivery system 100, such as an AED system 100, is illustrated in FIG. 1, and includes a defibrillator 102 and a plurality of electrodes 104. In the depicted embodiment, two electrodes 104a, 104b are provided; however, it will be appreciated that more than two electrodes 104 could be included with the system 100. Nonetheless, it will additionally be appreciated that generally only two electrodes 104 will be used at any given time when delivering a cardiac therapy pulse.

When the AED system 100 is used, the defibrillator 102 is coupled to a patient 106 via the electrodes 104a, 104b. In particular, the electrodes 104a, 104b are attached to the skin of the patient 106. In the depicted embodiment, one electrode 104a is attached to the upper right torso area of the patient 106, and the other electrode 104b is attached to the lower left torso area toward the side of the patient. It will be appreciated, however, that this is merely exemplary of one of various electrode attachment configurations. For example, the electrode 104a may alternatively be placed on the patient's chest area closer to the region of the heart, with the electrode 104b placed on the patient's back. As will be described in more detail further below, the electrodes 104a, 104b are used to both deliver a cardiac therapy pulse and to sense electrocardiogram (ECG) signals generated by the patient's heart.

Figure 2:
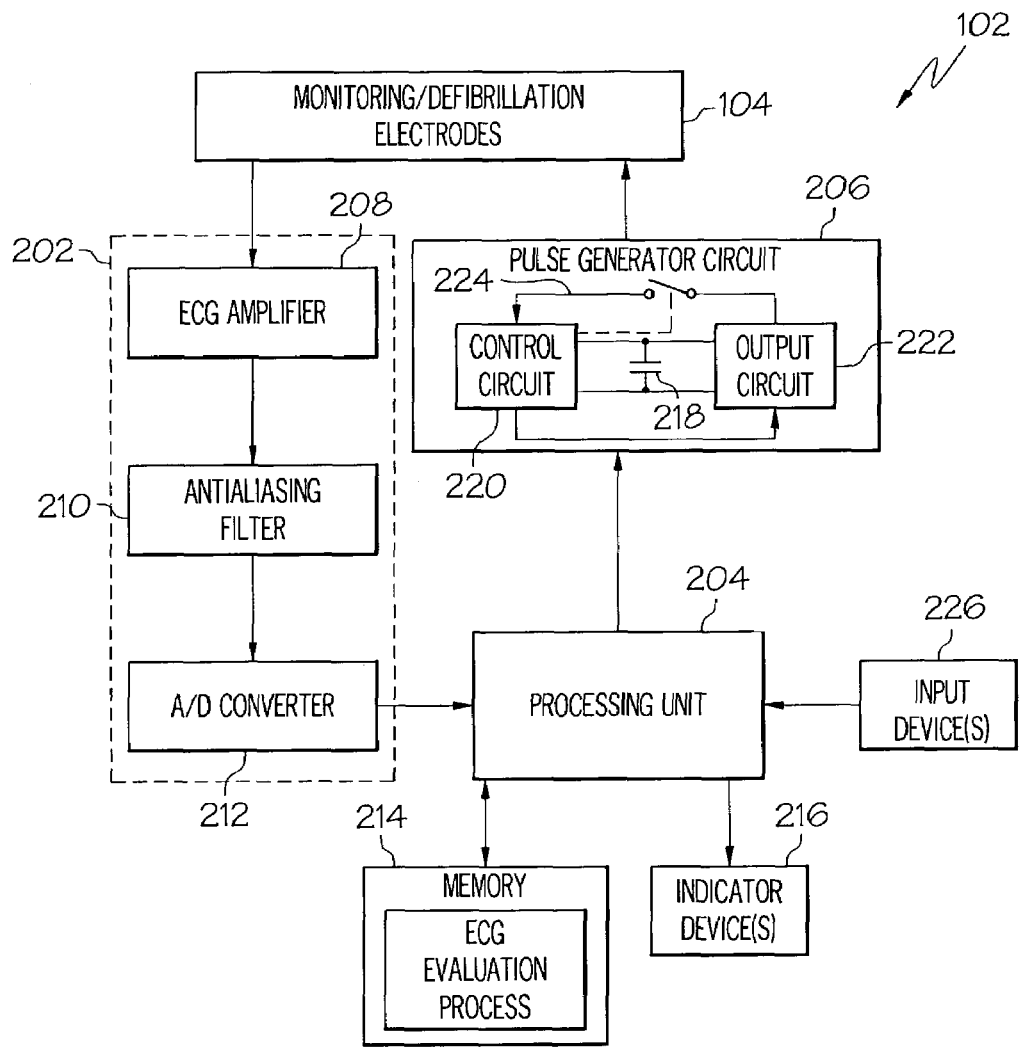
FIG. 2 is a block diagram depicting an exemplary circuit architecture of the external defibrillator of FIG. 1.

Turning now to FIG. 2, a description of an exemplary embodiment of the circuit architecture that may be implemented in the defibrillator 102 will be described. As FIG. 2 shows, the circuitry includes electrocardiogram (ECG) signal processor circuitry 202, a processor/controller 204, and pulse generator circuitry 206. The ECG signal processor circuitry 202 receives and appropriately processes ECG signals sensed by the electrodes 104a, 104b. To do so, the ECG signal processor circuitry 202, at least in the depicted embodiment, includes an ECG amplifier 208, an anti-aliasing filter 210, and an analog-to-digital (A/D) converter 212. The ECG amplifier 208 amplifies and filters the sensed ECG signals, to increase the power level of the sensed ECG signals and to eliminate noise and other signal contaminants. Thus, the ECG amplifier 208 may include, for example, both a low-pass filter and a high-pass filter that attenuate low and high frequencies, respectively, though it will be appreciated that various other types and/or filter configurations may be used.

The anti-aliasing filter 210 receives the amplified and filtered ECG signals from the ECG amplifier 208, and functions to remove the frequency components from the ECG signal that cannot be reliably sampled by the A/D converter 212, without introducing aliasing. The A/D converter 212 converts the sensed ECG signals, which are analog, into digital ECG data. The ECG data are then supplied to the processor/controller 204.

The processor/controller 204 evaluates the ECG data by implementing any one of numerous known ECG evaluation processes. An understanding of the various ECG evaluation processes that may be implemented by the processor/controller 204 is not needed to understand the invention, and will therefore not be described in detail. In the depicted embodiment, the ECG evaluation process evaluates the ECG data and determines, among other things, whether a cardiac therapy pulse should be delivered, and the desired energy level and type of the delivered pulse (e.g., either a defibrillation pulse or a pacing pulse). The processor/controller 204 is preferably a general purpose programmable microprocessor that operates in accordance with programmed instructions stored in memory 214, though it will be appreciated that it could be implemented in various other circuit architectures, including both analog and digital circuit architectures.

The processor/controller 204 preferably supplies one or more signals representative of the results of the ECG evaluation process to one or more indicator devices 216. The indicator devices 216 may be any one of numerous known indicator devices including, but not limited to, lights, a sound emitter to emit speech-related audible signals and/or non-speech-related audible signals, a printer, and/or a display screen. The information provided by the indicator devices 216 to the operator includes, for example, whether a cardiac therapy pulse should be delivered, and the desired energy level and type of the pulse. The indicator devices 216 may also be used to display a patient's ECG. The processor/controller 204 also provides one or more command signals to the pulse generator circuitry 206. The command signals instruct the pulse generator circuitry 206 to operate in either a defibrillation mode or a pacing mode.

In the depicted embodiment, the pulse generator circuitry 206 includes one or more energy storage capacitors 218, a control circuit 220, and an output circuit 222. In response to the command signals from the processor/controller 204, the control circuit 220 charges the energy storage capacitors 218 to a voltage magnitude. The voltage magnitude to which the processor/controller 204 commands the energy storage capacitors 218 to be charged depends, at least in part, on the results of the ECG evaluation process, and also on whether a defibrillation pulse or a pacing pulse needs to be delivered. The voltage magnitude to which the capacitors 218 are charged may vary between, for example, 100 volts and 2,000 volts or more. In addition to charging the capacitors 218, the control circuit 220 also controls the configuration and operation of the output circuit 222 in response to the command signals from the processor/controller 204. In particular, when the command signals from the processor/controller 204 instruct the pulse generator circuitry 206 to operate in the defibrillation mode, the output circuit 222 is configured and controlled to supply a defibrillation pulse by discharging the energy storage capacitors 218 in such a manner that the pulse generator circuitry 206 functions as a voltage source. The voltage magnitude of the defibrillation pulse to be supplied is determined, at least in part, from the sensed ECG signals.

Conversely, when the commands from the processor/controller 204 instruct the pulse generator circuitry 206 to operate in the pacing mode, the output circuit 222 is configured and controlled to supply a pacing pulse by discharging the energy storage capacitors 218 in such a manner that the pulse generator circuitry 206 functions as a current source. In the depicted embodiment, a feedback circuit 224 may be selectively coupled between the control circuit 220 and the output circuit 220, so that the pacing pulse is supplied at a substantially constant current magnitude. The current magnitude of the pacing pulse to be supplied is determined, at least in part, from the sensed ECG signals. It will be appreciated that the pulse generator circuitry configuration depicted and described, is merely one exemplary embodiment of the pulse generator circuitry 206, and that it could be implemented using any one of numerous circuit configurations to operate in both a defibrillation mode and a pacing mode, to thereby deliver both defibrillation pulses and pacing pulses, respectively. Various non-limiting exemplary circuit configurations are disclosed in U.S. Pat. No. 6,208,895, entitled "Circuit for Performing External Pacing and Biphasic Defibrillation," which is assigned to the assignee of the present application, and the entirety of which is hereby incorporated by reference.

The processor/controller 204 monitors the charging process and when the capacitors 218 are charged to the commanded voltage magnitude, the controller/processor 204 advises the operator via, for example, one or more of the indicator devices 216 that the defibrillator 102 is ready to deliver the pulse. The defibrillator 102 may be configured to deliver the pulse either automatically or in response to an input from an operator. If the defibrillator 102 is configured to automatically deliver the pulse, the processor/controller 204 commands the pulse generator circuitry 206 to discharge the energy storage capacitors 218 through the electrodes 104a, 104b, in either the defibrillation mode or the pacing mode, as appropriate, to thereby deliver a defibrillation pulse or a pacing pulse, respectively, as described above. If the defibrillator 102 is configured for manual delivery, one or more of the indicator devices 216, in response to a command from the processor controller 204, will request an operator to initiate pulse delivery. The operator may then initiate pulse delivery via, for example, an input device 226, which will result in the pulse generator circuitry 206 discharging the energy storage capacitors 218 through the electrodes 104a, 104b, in either the defibrillation mode or the pacing mode, to thereby deliver a defibrillation pulse or a pacing pulse, respectively. The input device 226 may include one or more keys, knobs, buttons, or other types of user input mechanisms.

Figure 3:
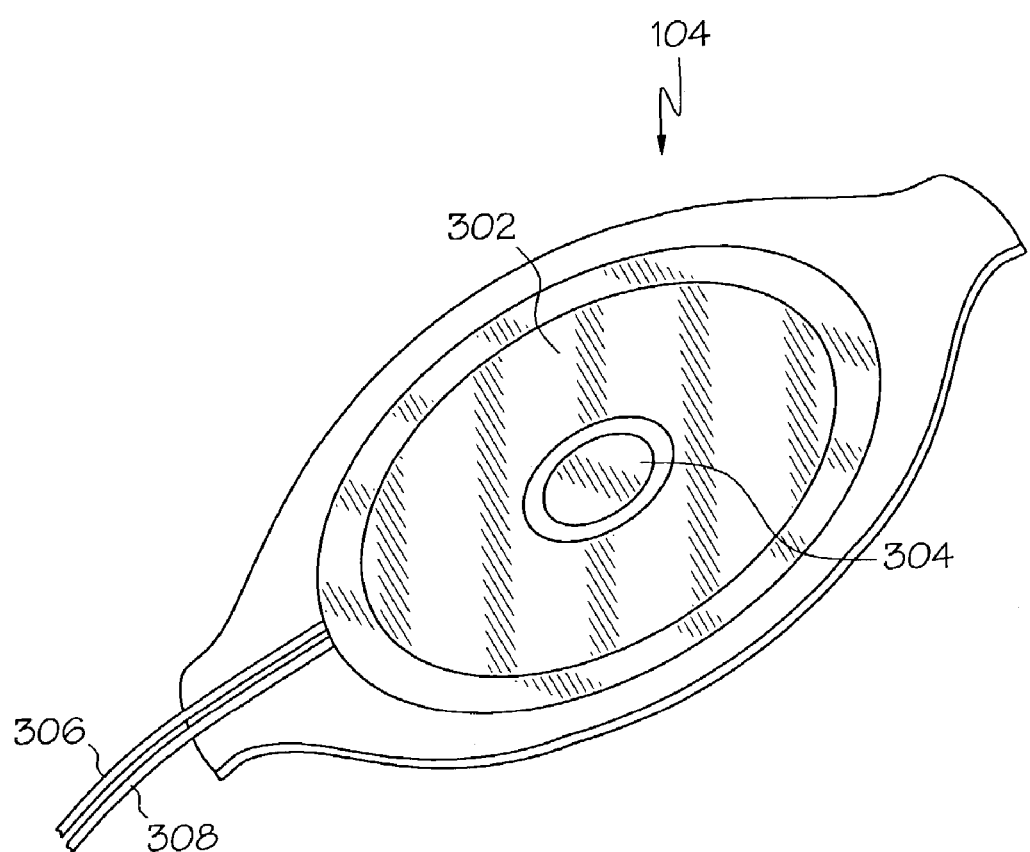
FIG. 3 is a perspective view of an electrode according to an exemplary embodiment of the present invention that may be used with the external defibrillator of FIG. 1.

With reference now to FIG. 3, a detailed description of an exemplary embodiment of the electrodes 104 will be provided. For convenience and ease of explanation, only a single electrode 104 is shown in FIG. 3. In the depicted embodiment, the electrodes 104 each include two conductive elements, a therapy element 302 and a monitor element 304, which are electrically insulated from one another. The therapy element 302 is adapted to be electrically coupled to the pulse generator circuitry 206 via a first lead 306, and is used to receive therapy pulses generated in the pulse generator circuitry 206 and deliver the therapy pulses to a patient. The monitor element 304 is adapted to be electrically coupled to the ECG processor circuitry 202 via a second lead 308, and is used to detect and supply patient ECG signals to the ECG processor circuitry 202. The therapy element 302 is preferably configured to have a larger surface area than the monitor electrode 304. Although not depicted in FIG. 3, it will be appreciated that the first 306 and second 308 leads for all of the electrodes 104 could form part of, or be connected to, a single multi-lead cable that connects to the defibrillator 102. It will additionally be appreciated that the first 306 and second 308 leads could be appropriately connected within the defibrillator 102, and the defibrillator 102 could be appropriately configured, such that the therapy elements 302 and the monitor elements 304 are electrically coupled in parallel when a therapy pulse is being delivered. Doing so can reduce the overall impedance of the electrodes 104 during pulse delivery.

The therapy 302 and monitor 304 elements may be formed of any one of numerous conductive metals or metal alloys such as, for example, copper or tin. The metal or metal alloy used for the therapy 302 and monitor elements 304 could be the same or different. Although the electrode 104 is depicted as including only one therapy element 302 and one monitor element 304, it should be appreciated that the electrode could include more than this number of therapy 302 and/or monitor 304 elements. Moreover, though not depicted, it will be appreciated that the therapy element 302 and monitor element 304 may each be adhered to a common substrate such as, for example, a flexible foam backing layer, with a medical grade adhesive, and may each be covered with a suitable conductive gel. It will be appreciated that the conductive gel could be continuous over the entire electrode surface or, preferably, have a gap between the gel that covers the therapy element 302 and the gel that covers the monitor element 304. It will additionally be appreciated that the conductive gel used to cover the therapy 302 and monitor 304 elements could be the same gel or different types of conductive gels.

As was noted above, the defibrillator 102 may supply therapy pulses of varying voltage and/or current magnitudes, depending upon whether the patient needs to receive, for example, a defibrillation pulse or a pacing pulse. In addition, the defibrillator 102 may be configured to supply the therapy pulses at a predetermined rate, which may be varied, and which allows, for example, transthoracic pacing pulses to be administered to a patient. No matter the voltage or current magnitude of the supplied pulse, the therapy element 302 on each electrode 104 will accumulate an electrostatic charge during pulse delivery. However, because each electrode 104 includes a separate monitor element 304 that is electrically insulated from the therapy element 302, the monitor elements 304 will not accumulate a charge and can, therefore, detect a patient's ECG signals substantially immediately after, or a very short time after, a cardiac therapy pulse has been delivered. Thus, the electrodes 104 may be used to accurately monitor a patient's ECG signals between pulses when the system 100 is being used, for example, to supply transthoracic pacing pulses.

With the above-described capabilities, the defibrillator 102 may be configured so that, for example, the processor/controller 204 commands the pulse generator circuitry 206 to deliver an initial defibrillation pulse at an initial voltage magnitude or an initial pacing pulse at an initial current magnitude. Thereafter, based at least in part on the ECG data, the processor/controller 204 may then command the pulse generator circuitry 206 to incrementally increase or decrease the defibrillation pulse voltage magnitude or the pacing pulse current magnitude. This incremental adjustment will cease when the processor/controller 204 determines, based at least in part on the ECG data, that an appropriate defibrillation voltage or pacing current magnitude is reached. It will be appreciated that throughout the operation of the system 100, the processor/controller 204 will function to substantially continuously determine the appropriate voltage or current magnitude of the therapy pulse to be delivered, and command the pulse generator circuitry 206 to deliver therapy pulses at the appropriate voltage or current magnitude. It will additionally be appreciated that throughout the operation of the system 100, the processor/controller 204 will function to substantially continuously determine the appropriate therapy pulse duration (e.g., pulse width) and periodicity, and command the pulse generator circuitry 206 appropriately.

The system and method described herein allows ECG signals to be accurately monitored during cardiac therapy pulse delivery and/or allows ECG signals to be accurately detected substantially immediately after a cardiac therapy pulse has been delivered without relying on additional ECG monitoring leads. Thus, cardiac therapy pulses can be automatically delivered to a patient at the appropriate magnitude, duration, and frequency.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of monitoring electrocardiogram (ECG) signals during cardiac therapy pulsing, comprising:
   applying two or more electrodes to a patient, each electrode having at least a therapy element and a monitor element coupled thereto;
   supplying one or more cardiac therapy pulses to the therapy element on each of the applied electrodes;
   monitoring one or more ECG signals via the monitor element on each of the applied electrodes; and
   electrically coupling the therapy element and the monitor element on one or more of the electrodes in parallel with one another when supplying the cardiac therapy pulses.

2. A cardiac pulse therapy delivery system comprising:
   a plurality of electrodes, each electrode having at least one therapy element and at least one monitor element electrically insulated from one another;
   an electrocardiogram (ECG) signal processor circuit electrically coupled to each monitor element on each electrode and operable to convert ECG signals detected by the monitor elements into ECG data;
   a pulse generator circuit electrically coupled to each therapy element on each electrode and supplying one or more cardiac therapy pulses to the therapy element on each of the applied electrodes operable to supply one or more cardiac therapy pulses thereto; and
   a processor coupled to receive the ECG data from the ECG signal processor circuit and operable, in response thereto, to determine whether one or more additional cardiac therapy pulses is needed;
   wherein the processor is further operable to selectively electrically couple the therapy element and the monitor element on each electrode in parallel with one another.

3. The system of claim 2 wherein the processor electrically couples the therapy element and the monitor element on each electrode in parallel with one another when the cardiac therapy pulse supplied by the pulse generator circuit is a defibrillation pulse.

* * * * *

UNITED STATES PATENT AND TRADEMARK OFFICE
CERTIFICATE OF CORRECTION

PATENT NO. : 7,486,990 B2  
APPLICATION NO. : 10/423602  
DATED : February 3, 2009  
INVENTOR(S) : Joseph L. Sullivan It is certified that error appears in the above-identified patent and that said Letters Patent is hereby corrected as shown below:

Column 3, line 45, "configured to operate in accordance with an the present" should read
-- configured to operate in accordance with the present --

Column 8, line 48, "3. The system of claim 2 wherein the processor" should read
-- 3. The system of claim 2, wherein the processor --

Signed and Sealed this
Sixteenth Day of August, 2011

David J. Kappos
*Director of the United States Patent and Trademark Office*